United States Patent [19]

Braish et al.

[11] Patent Number: 5,523,413

[45] Date of Patent: Jun. 4, 1996

[54] PROCESS FOR OPTICALLY ACTIVE 2-ALKYL-2,5-DIAZABICYCLO[2.2.1] HEPTANES

[75] Inventors: Tamim F. Braish; Darrell E. Fox, both of New York, N.Y.

[73] Assignee: Pfizer Inc., New York, N.Y.

[21] Appl. No.: 526,619

[22] Filed: Sep. 11, 1995

Related U.S. Application Data

[62] Division of Ser. No. 300,776, Sep. 6, 1994, Pat. No. 5,475, 177, which is a division of Ser. No. 896,291, Jun. 10, 1992, Pat. No. 5,371,235, which is a division of Ser. No. 797,883, Nov. 26, 1991, Pat. No. 5,157,125, which is a division of Ser. No. 621,414, Jan. 10, 1981, Pat. No. 5,095,121, which is a division of Ser. No. 453,365, Dec. 21, 1989, Pat. No. 5,013,839, which is a continuation of Ser. No. 412,072, Sep. 25, 1989, abandoned.

[51] Int. Cl.[6] .................. C07D 207/16; C07D 207/12

[52] U.S. Cl. ............................................. 548/532; 548/530

[58] Field of Search ................................. 548/532, 530

[56] References Cited

U.S. PATENT DOCUMENTS

| 4,264,620 | 4/1981 | Iwao et al. | 548/532 |
| 5,196,548 | 3/1993 | Braish et al. | 548/532 |

*Primary Examiner*—David B. Springer
*Attorney, Agent, or Firm*—Peter C. Richardson; Paul H. Ginsburg; Bryan C. Zielinski

[57] ABSTRACT

1S,4S and 1R,4R-2-Alkyl-2,5-diazabicyclo[2.2.1]-heptanes useful as intermediates in the synthesis of certain antibacterial quinolones, are prepared respectively, from trans-4-hydroxy-L-proline and trans-4-hydroxy-D-proline via multistep procedures.

12 Claims, No Drawings

PROCESS FOR OPTICALLY ACTIVE 2-ALKYL-2,5-DIAZABICYCLO[2.2.1] HEPTANES

This is a division of application Ser. No. 08/300,776 filed Sep. 6, 1994 now U.S.Pat. No. 5,475,177; which is a division of application Ser. No. 07/896,291 filed Jun. 10, 1992, now U.S. Pat. No. 5,371,235; which is a division of application Ser. No. 07/797,883 filed Nov. 26, 1991, now U.S. Pat. No. 5,157,125; which is a division of application Ser. No. 07/621,414 filed Jan. 8, 1991, now U.S. Pat. No. 5,095,121; which is a division of application Ser. No. 07/453,365 filed Dec. 21, 1989, now U.S. Pat. No. 5,013,839; which is a continuation of application Ser. No. 07/412,072 filed Sep. 25, 1989, now abandoned.

BACKGROUND OF THE INVENTION

This invention relates to the preparation of 1S,4S- and 1R,4R-2-alkyl-2,5-diazabicyclo [2.2.1]-heptane intermediates having utility in the preparation of antibacterial quinolones such as those disclosed in U.S. Pat. No. 4,775,668.

A method for the synthesis of 2,5-diazabicyclo[2.2.1] heptanes has been described by Portoghese et al., J. Org. Chem., 31, 1059 (1966). According to this method, hydroxy-L-proline is transformed into tritosylhydroxy-L-prolinol which is first reacted with benzylamine and then with hydrogen iodide, phosphorus, and acetic acid to form N-benzyl-2,5-diazabicyclo[2.2.1]heptane dihydroiodide. U.S. Pat. No. 3,947,445 follows a similar procedure and then converts the dihydroiodide through a three step procedure into 2-methyl-2,5-diazabicyclo[2.2.1]heptane.

In our prior copending application, Ser. No. 350,423, filed May 11, 1989, we describe another method for the preparation of said optically active 2,5-diaza-2-alkylbicyclo [2.2.1]heptanes of the formula (IX) below from trans-4-hydroxy prolines of the formula (I) below.

SUMMARY OF THE INVENTION

The over-all processes of the present invention for the preparation of optically active 2,5-diaza-2-alkylbicyclo [2.2.1]heptanes (IX) from 4-hydroxyproline (I) are shown in Schemes I and II. In these schemes, all of the compounds depicted are chiral and optically active. Viewed as formulas which depict absolute stereochemistry, they depict, for example, trans-4-hydroxy-L-proline, also known simply as hydroxyproline, of the formula (I), and (1S,4S)-2-alkyl 2,5-diaza[2.2.1]heptanes, of the formula (IX). Viewed as formulas which depict relative stereochemistry, they also depict the corresponding enantiomers, for example, trans-4-hydroxy-D-proline (I) and (1R,4R)-2-alkyl-2,5-diaza [2.2.1]heptanes (IX). In these formulas R, $R^1$ and $R^3$ are each independently $(C_1-C_6)$alkyl;

$R^2$ and $R^4$ are each independently $(C_1-C_6)$alkyl, trifluoromethyl or

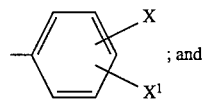 ; and

X and $X^1$ are each independently hydrogen, $(C_1-C_6)$alkyl, bromo, chloro, trifluoromethyl, methoxy or nitro.

In particular, the present invention is directed to the process steps:

(VII)→(VIII) [carried out by the agency of at least one molar equivalent of an alkali metal carbonate salt in a reaction inert solvent];

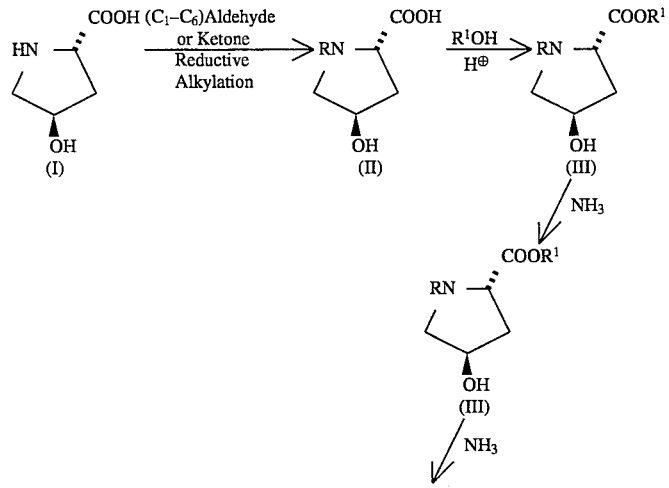

Scheme I

-continued
Scheme I

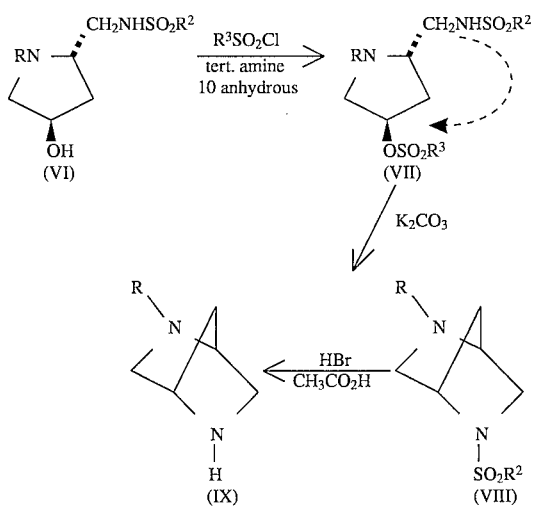

Scheme II

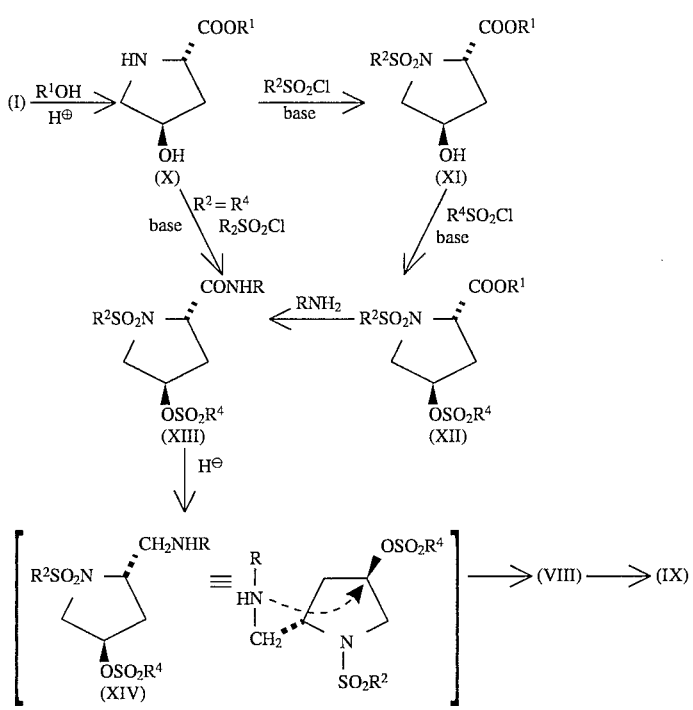

(VII)→(VIII)→(IX);
(I)→(II)→(III)→(IV)→(V)→(VII)→(VIII);
(XIII)→[(XIV)]→(VIII) [carried out by the agency of a hydride reducing agent in a reaction inert solvent, without isolation of the intermediate amine];
(XIII)→[(XIV)]→(VIII)→(IX); and
(I)→(X)→(XII)→(XIII)→[(XIV)]→(VIII).

The expression "reaction inert solvent" refers to a single or multicomponent solvent, the component(s) of which do not interact with starting materials, reagents, intermediates or products in a manner which adversely affects the yield of the desired product.

In the conversion of (VII) to (VIII), the preferred reagent is $K_2CO_3$ and the preferred solvent is a lower alcohol, particularly methanol. In the conversion of (XV) to (IX), the preferred hydride reducing agent is $LiAlH_4$ and the preferred solvent is an ether, particularly diethylether or tetrahydrofuran.

In these processes, the preferred values of R and $R^3$ are each methyl; of $R^1$ is methyl or ethyl; and of each of $R^2$ and $R^4$ is methyl or 4-methylphenyl. Because the number of steps is reduced, it is preferred that $R^2$ and $R^3$ or $R^4$ have the same value.

The present invention is also directed to optically active intermediates of the relative or absolute stereochemical formulas

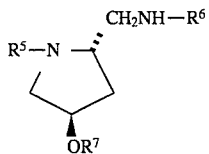   (XV)

wherein in a first alternative, $R^5$ is $(C_1-C_6)$alkyl;

$R^6$ is $SO_2R^2$;

$R^2$ is as defined above;

$R^7$ is hydrogen or $SO_2R^3$; and $R^3$ is as defined above; or in a second alternative, $R^6$ is $(C_1-C_6)$ alkyl;

$R^5$ is $SO_2R^2$;

$R^2$ is as defined above;

$R^7$ is $SO_2R^4$; and $R^4$ is as defined above;

and

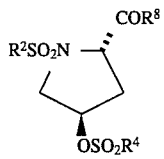   (XVI)

wherein $R^2$ and $R^4$ are defined above;

$R^8$ is $OR^1$ or NHR; and

R and $R^1$ are as defined above.

The preferred compounds of the formula (XV) are in the first alternative having $R^5$ as methyl, $R^2$ as methyl or 4-methylphenyl, and, when $R^7$ is $SO_2R^3$, $R^3$ as methyl;

and in the second alternative having $R^6$ as methyl, and $R^2$ and $R^4$ as methyl or 4-methylphenyl.

The preferred compounds of the formula (XVI) have R as methyl, $R^1$ as methyl or ethyl, and $R^2$ and $R^4$ the same and as methyl or 4-methylphenyl.

DETAILED DESCRIPTION OF THE INVENTION

The various process steps of the present invention are readily carried out.

The initial step according to Scheme I involves conventional reductive alkylation of a transhydroxyproline (I) with a $(C_1-C_6)$ aliphatic aldehyde or ketone appropriate to the desired N-alkyl substituent (e.g., formaldehyde→methyl, hexanal→hexyl, acetone→isopropyl). This reductive alkylation is carried out under typical hydrogenation conditions, best over a noble metal catalyst, preferably palladium. The catalyst can be a noble metal per se, or an oxide or salt, reduced to the active metal catalyst under the conditions of hydrogenation, or a noble metal catalyst on a support such as carbon or alumina. In the present instance the most preferred catalyst is Pd/C. The reaction inert solvent includes water, an organic solvent such as ethanol or a mixed solvent such as aqueous alcohol. When R is methyl, the preferred source of formaldehyde is simply aqueous formaldehyde and in this case water alone is the preferred solvent. At least one molar equivalent of the aldehyde or ketone is usually employed, and when this reagent (like formaldehyde) is readily available it can be employed in large excess in order to reduce reaction time and maximize the stoichiometric yield from the generally more valuable hydroxyproline. Temperature is not critical, temperatures of 0°–50° C. being generally satisfactory, and ambient temperature, avoiding the cost of heating or cooling, is most preferred. Likewise, pressure is not critical, but low to moderate pressures (e.g., 1–8 atmospheres) are preferred in order to avoid the need for expensive, high pressure reactors.

The second step in Scheme I (II→III) involves conventional conversion of a carboxylic acid group to a $(C_1-C_6)$carboxylate ester, preferably accomplished by simple strong acid catalyzed esterification with an alcohol, usually employed in gross excess and also as solvent. Suitable strong acids are such as HCl, $H_2SO_4$, and $R^2SO_3H$ $R^2$ where is defined as above, are generally employed in anhydrous or near anhydrous form in amounts ranging from truly catalytic (e.g., 10 mol %), but generally in excess of the 100 mol % necessary to neutralize the tertiary amine group. Temperature is not critical, 0°–50° C. being generally satisfactory and room temperature particularly convenient.

In the third step of Scheme I (III→IV), the lower alkyl ester group is conventionally converted to a carboxamide group by the action of ammonia in a reaction inert solvent. When water is the solvent, undiluted, concentrated ammonia is preferred. When the solvent is a lower alcohol such as methanol, anhydrous ammonia, saturated into the solvent, is preferred. Temperature is not critical, 0°–50° C. being generally satisfactory, with ambient temperatures being especially convenient.

In the fourth step of Scheme I, the carbamoyl group in (IV) is reduced with a hydride reducing agent to the aminomethyl group in (V). Hydride reducing agents, such as diisobutyl aluminum hydride or lithium aluminum hydride which show a high level of activity in reducing amides to amines, are preferred reagents in this reduction. It is preferred to use an excess of these reagents, e.g., as many as 6 mols of diisobutyl aluminum hydride or 1.5 mols of lithium aluminum hydride per mole of amide. The reduction is carried out in a reaction inert solvent, usually an ether such as diethylether or tetrahydrofuran. Temperature is not critical, 0°–50° C. generally being satisfactory and ambient temperatures most preferred.

In Scheme I, when $R^2$ and $R^3$ are different, the conversion of (V) to (VII) will require two steps. In the first of these, the sulfonamide is best selectively formed by acylation of the amine with substantially one molar equivalent of the appropriate sulfonyl chloride in the presence of a sufficient amount of a base (such as n-butyllithium) to neutralize co-produced hydrogen chloride, in a reaction inert solvent, suitably an ether such as tetrahydrofuran. This reaction is generally carried out at a reduced temperature (e.g., –50° to +15° C.), a temperature near the middle of this range (e.g., –10° to –15° C.), being particularly satisfactory. In this case, subsequent O-sulfonylation (VI→VII) is readily accomplished using at least one molar equivalent of $R^2SO_2Cl$ in the presence of at least one molar equivalent of a tertiary amine such as triethylamine, generally in an aprotic solvent such as an ether (e.g., tetrahydrofuran). Temperature in this second stage is not critical, with a temperature in the range of 0°–50° C. generally satisfactory and ambient temperature usually preferred.

As noted above in the preferred routes $R^2$ and $R^3$ are the same, in which case concurrent N- and O-sulfonylation is readily accomplished under the latter conditions, except that at least two equivalents each of the sulfonylchloride ($R^3SO_2Cl$) and the tertiary amine are employed.

At the heart of the present invention is the cyclization of the bis-sulfonylated derivative (VII) to form the 2-alkyl-5-(alkane- or benzene-)sulfonyl derivative (VIII). This cyclization is readily accomplished by the agency of at least one molar equivalent of an alkali metal carbonate (e.g., $K_2CO_3$ is particularly well-suited) in a reaction inert solvent such as a lower alcohol (e.g., methanol is particularly well-suited).

In the first step of Scheme II, the hydroxyproline (I) is converted to the ester (X) best accomplished by the methods described above for the esterification of N-alkylhydroxyprolines (II→III). Bis-sulfonylation of (X) to form the compound of the formula (XII) and its ammonolysis to the amide (XIII) are also accomplished by the methods described above, except that the amine $RNH_2$ is substituted for $NH_3$.

However, in marked contrast to Scheme I, in Scheme II, the hydride reduction of the carbamoyl group to an alkylamino group and cyclyzation are now accomplished in a single step, viz., by the action of hydride reducing agent as described above, with the expected product, (XIV), spontaneously cyclyzing to form the desired 2-alkyl-5-alkane- or benzenesulfonyl derivative (VIII).

Finally, in order to form the amine (IX), according to either Scheme, the N-sulfonyl group is removed by conventional reductive or hydrolytic methods. This is best accomplished with HBr in acetic acid as reagent, conveniently with isolation of (IX) in the form of its dihydrobromide salt. Again temperature is not critical, 0°–50° C. being fully satisfactory and ambient temperature generally preferred. Those skilled in the art will understand that sodium in liquid ammonia represents an alternative reductive method for removal of the sulfonyl group, while use of strong aqueous acid (HCl $H_2SO_4$, etc.) represents an alternative hydrolytic method for its removal.

The starting materials required in the operation of the present invention are readily available. Thus, trans-hydroxy-L-proline is a natural aminoacid which is commercially available, while its enantiomer is available according to the method of Baker, et al., J. Org. Chem., 46, pp. 2954–2960 (1981).

The amines of the formula (IX) are used as the source of side chain in the preparation of certain antibacterial quinolones such as those disclosed in U.S. Pat. No. 4,715,668, cited above.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979.

EXAMPLE 1 trans -N-Methyl-4-hydroxy-L-proline (II, R=CH$_3$)

To 40 g (305 mmol) of trans-4-hydroxy-L-proline in 80 ml of water was added 80 ml of 30% aqueous formaldehyde solution and 7.0 g of 5% palladium on carbon catalyst (50% wet), and the mixture was hydrogenated at 50 psig using a Parr Shaker. After 24 hours, the catalyst was recovered by filtration over diatomaceous earth and the filtrate evaporated under reduced pressure to provide 43.5 g (98.3%) of title product; mp 140°–142° C. (decomposition); $^1$H-NMR (D$_2$O): 4.65 (m, 1H), 4.20 (dd, 1H), 3.97 (dd, 1H), 3.2 (dm, 1H), 2.50 (m, 1H), 2.25 (m, 1H); [alpha]$_D$=–54.8° (c=1.18, H$_2$O).

By the same method, trans-4-hydroxy-D-proline is converted to enantiomec trans-N-methyl-4-hydroxy-D-proline, having identical properties except for sign of rotation.

EXAMPLE 2 trans-N-Methyl-4-hydroxy-L-proline Methyl Ester (III, R=R$^1$=CH$_3$)

Title product of the preceding Example (100 g, 690 mmol) was suspended in 600 ml of methanol and anhydrous HCl gas was bubbled through the reaction mixture until it became homogeneous. The reaction was then heated to reflux for 16 hours, after which it was cooled and the solvent was replaced with 150 ml of water. 200 g (1.44 mol) of potassium carbonate was then added carefully at 0° C. and the product was extracted with 4×200 ml portions of ethyl acetate. The combined organic layers were dried (Na$_2$SO$_4$) and evaporated to provide 87 g (72%) of product as a white solid; mp 53°–54° C.; $^1$H-NMR(D$_2$O) 4.85 (s, 3H), 4.73 (m, 2H), 3.90 (s, 3H, N-methyl), 3.58 (m, 1H), 3.45 (m, 1H), 2.54 (m, 1H), 2.37 (m, 1H); [alpha]$_D$=–80.0° (c=1.038, CH$_3$OH).

By the same method, the enantiomeric product of the preceding Example is converted to the enantiomer of present title product, having identical properties except for sign of rotation.

EXAMPLE 3

(2 S,4R)-1-Methyl-2-carbamoyl-4-hydroxypyrrolidine (IV, R=CH$_3$)

Title product of the preceding Example (20 g, 126 mmol) was dissolved in 40 ml of ice cold, saturated NH$_4$OH, and the resulting solution then warmed to room temperature. After stirring for 24 hours the solvent was removed under high vacuum to produce a quantitive yield of present title product as a white, crystalline solid; mp 138°–140° C.; Anal. C 49.99, H 8.40, N 18.27; calcd. C 49.97, H 8.40, N 19.43; $^1$H-NMR (D$_2$O) 4.43 (m, 1H), 3.42 (dd, 1H), 3.25 (AB pattern, 1H), 2.36 (s, 3H), 2.33 (M, 1H), 2.1 (m, 2H); [alpha]$_D$=–105.48° (c=0.953, CH$_3$OH).

By the same method, the enantiomeric product of the preceding Example is converted to the enantiomer of present title product, having identical properties except for sign of rotation.

EXAMPLE 4

(2 S,4R)-1-Methyl-2-aminomethyl-4-hydroxypyrrolidine (V, R=CH$_3$)

Title product of the preceding Example (15 g, 104 mmol) was suspended in 75 ml of tetrahydrofuran and 572.5 ml (572.5 mmol) of diisobutyl aluminum hydride (1M solution in hexanes) was added over a period of 15 minutes. The mixture was then heated to reflux for two days and judged complete by monitoring with thin layer chromatography. Diatomaceous earth (30 g) was then added to the reaction and while cooling with an ice bath, 300 ml of methanol was added dropwise. The slurry was then filtered and the solvents were evaporated to provide 8.1 g of a colorless oily product (60%); $^{13}$C-NMR (D$_2$O) 69.5 (CH), 66.8 (CH), 64.9 (CH$_2$), 44 0 (CH$_2$), 41.0 (CH$_3$), 39.5 (CH$_2$); [alpha]$_D$=−61.94° (c=0.956, CH$_3$OH).

By the same method, the enantiomeric product of the preceding Example is converted to the enantomer of present title product, having identical properties except for sign of rotation.

EXAMPLE 5

(2S,4R)-1-Methyl-2-[(4-methylbenzenesulfonylamino)methyl]-4-hydroxypyrrolidine (VI, R=CH$_3$, R$^2$=p-CH$_3$C$_6$H$_4$)

To title product of the preceding Example (7.3 g, 56.2 mmol) in 200 ml of tetrahydrofuran at −10° C. was added 22.46 ml of n-butyllithium (56.2 mmol, 2.5M in hexanes) over a period of 30 minutes. p-Toluene-sulfonyl chloride (10.2 g, 53.3 mmol) in 10 ml of tetrahydrofuran was then added. After stirring the mixture for two hours at −10° C., 20 ml of water were added and the reaction was extracted with 2×140 ml of methylene chloride. The combined organic layers were dried (Na$_2$SO$_4$) and evaporated at reduced pressure to provide 15 g (94.3%) of present title product as a light yellow oil; $^{13}$C-NMR (CDCl$_3$) 143.4, 136.5, 129.7, 127.0, 69.1, 64.7, 62.4, 43.0, 40.0, 38.2, 21.5; [alpha]$_D$=−34.67° (c=0.90, CH$_3$OH).

EXAMPLE 6

(2S,4R)-1-Methyl-2-[(4-methylbenzensulfonylamino)-methyl]-4-(methanesulfonyloxy)pyrrolidine (VII, R=R$^3$=CH$_3$, R$^2$=pCH$_3$C$_6$H$_4$)

To title product of the preceding Example (1.0 g, 3.5 mmol) in 20 ml of tetrahydrofuran was added 0.49 ml (3.5 mmol) of triethylamine and 0.27 ml (3.5 mmol) of methanesulfonyl chloride. After stirring at room temperature for 30 minutes, 20 ml of water were added and the reaction was extracted with 2×40 ml of methylene chloride. The combined organic layers were then dried (Na$_2$SO$_4$) and evaporated under reduced pressure to provide 1.2 g (94%) of product as an oil; $^1$H-NMR (CDCl$_3$) 7.73 (d, 2H), 7.40 (d, 2H), 5.04 (m, 1H), 3.70 (m, 1H), 3.55 (dd, 1H), 3.05 (m, 1H), 3.0 (s, 3H), 2.83 (m, 1H), 2.62 (dd, 1H), 2.40 (s, 3H), 2.23 (s, 3H), 2.10 (m, 1H), 1.82 (m, 1H).

EXAMPLE 7

(2S,4R)-1-Methyl-2-[(methanesulfonylamino)methyl]-4-methanesulfonyloxypyrrolidine (VII, R=R$^2$=R$^3$=CH$_3$)

To title product of Example 4 (100 mg, 0.76 mmol) in 2 ml of tetrahydrofuran was added 0.21 ml (1.52 mmol) of triethylamine and 0.118 ml (1.52 mmol) of methanesulfonyl chloride and the mixture was allowed to stir at 0° C. for one hour and at room temperature for an additional hour. Then 2 ml of water were added and the mixture was extracted with 2×2 ml of methylene chloride. The combined organic layers were dried (MgSO$_4$) and evaporated under reduced pressure to provide 140 mg (64%) of present title product as an oil; $^1$H-NMR (CDCl$_3$) 5.05 (m, 1H), 3.50 (dd, 1H), 3.17 (m, 1H), 3.0 (s, 3H), 2.95 (s, 3H), 2.80 (m, 1H), 2.58 (dd, 1H), 2.30 (s, 3H), 2.25–2.1 (m, 3H). CMR(CDCl$_3$): 78.4, 6 2.3, 61.9, 42.5, 40.1, 39.8, 38.2, 35.4.MS: M+1 287 (20), 191 (17), 178 (100).

By the same method, the enantiomeric product of Example 4 is converted to (2R,4S)-1-methyl-2-[(methanesulfonylamino)methyl]- 4-methanesulfonyloxypyrrolidine.

EXAMPLE 8

(1S,4S)-2-Methyl-5-(4-methylbenzenesulfonyl)-2,5-diazabicyclo[2.2.1]heptane (VIII, R=CH$_3$, R$^2$=pCH$_3$C$_6$H$_4$)

To title product of Example 6 (760 mg, 5.52 mmol) was added 760 mg (5.52 mmol) of K$_2$CO$_3$. After stirring the mixture for 24 hours, the solvent was removed under reduced pressure and 20 ml of water were added. The aqueous layer was then extracted with 2×40 ml of methylene chloride and the combined organic layers were dried (MgSO$_4$) and evaporated under reduced pressure to provide 470 mg (64%) of present title product as solid; mp 87°–88° C.; $^{13}$C-NMR (CDCl$_3$) 143.5, 135.4, 129.8, 127.4, 62.9, 61.1, 61.0, 49.9, 40.2, 34.9, 21.5. Anal. C 58.73, H 6.90, N 10.51, S 12.26, calcd. C 58.62, H 6.81, N 10.52, S 12.04; [alpha]$_D$=+18.69° (c=1.18, CH$_3$OH).

EXAMPLE 9

(1S,4S)-2-(Methanesulfonyl)-5-methyl-2,5-diazabicyclo[2.2.1]heptane (VIII, R=R$^2$=CH$_3$)

By the method of the preceding Example, title product of Example 7 (110 mg, 0.38 mmol) was converted to present title product as an oil, purified by chromatography on silica gel; 44 mg (60%); $^1$H-NMR (CDCl$_3$) 4.27 (m, 1H), 3.55 (dd, 1H), 3.5 (s, 3H), 3.20 (dd, 1H), 2.84 (m, 3H), 1.92 (m, 1H), 1.71 (m, 1H); $^{13}$C-NMR (CDCl$_3$): 63.1, 61.4, 60.6, 50.6, 40.8, 38.5, 35.7.

By the same method, the enantiomeric product of Example 7 is converted to (1R,4R)-2-(methanesulfonyl)-5-methyl-2,5-diazabicyclo[2.2.1]heptane.

EXAMPLE 10

(1S,4S)-2-Methyl-2,5-diazabicyclo[2.2.1]heptane (IX, R=CH$_3$)

Title product of Example 8 (60 g, 225 mmol) was suspended in 900 ml of 30% HBr in CH$_3$COOH, stirred for six hours at room temperature, then reduced to ¼ volume at the water aspirator, the residue diluted with 1800 ml of ethyl acetate, and the resulting precipitated solids recovered by filtration. These solids were recrystalized by dissolving in the minimum necessary CH$_3$OH at reflux, cooling and the addition of 400 ml of isopropyl alcohol to yield 48 g (81%) of present, purified title product; mp 258–°259° C.; $^1$H-NMR (D$_2$O) 4.73 (m, 1H), 4.62 (m, 1H), 3.8–3.6 (m, 4H), 3.08 (s, 3H), 2.65 (m, 1H), 2.35 (m, 1H); [alpha]$_D$=+13.21° (c=0. 946, CH$_3$OH).

By the same method, the title product of Example 9 is also converted to present title product, and the enantiomeric product of Example 9 is converted to (1R,1R)-2-methyl-2,5-diazabicyclo[2.2.1]heptane.

EXAMPLE 11 trans-4-Hydroxy-L-proline Methyl Ester Hydrochloride (X, R$^1$=CH$_3$)

Anhydrous HCl was bubbled through a stirred suspension of trans-4-hydroxy-L-proline (80 g, 0.61 mol) in 500 ml anhydrous methanol until the mixture was homogeneous.

The reaction was heated to reflux for five hours, and the volume of the solvent then reduced by one half. Ether (100 ml) was added, and the mixture kept in a freezer overnight. The resulting precipitate was filtered, washed with ether and dried under reduced pressure to yield 111 g of present title product (93% yield). mp 170°–172° C.

By the same method trans-4-hydroxy-D-proline is converted to the enantiomer of present title product.

EXAMPLE 12

Methyl (2S, 4R)-1-(4-Methylbenzenesulfonyl)-4-(4-methylbenzenesulfonyloxy)pyrrolidine-2-carboxylate (XII, $R^1$=$CH_3$, $R^2$=$R^4$=p$CH_3C_6H_4$)

Title product of the preceding Example (15 g, 83.1 mmol) was stirred with 150 ml pyridine and 11.5 ml of triethylamine at 0° C. for 30 minutes. p-Toluenesulfonyl chloride (34.8 g, 181.9 mmol) was added portionwise, maintaining a temperature of 0°–5° C. The mixture was stirred 18 hours at 0° C., then added to two volumes of ice cold water, stirred at room temperature for one hour, and present title product recovered by filtration and dried in vacuo at 30° C. for 48 hours to yield 38 g (99%) of present title product, mp 94°–95° C.

By the same method, the enantomeric product of the preceding Example is converted to the enantiomer of present title product.

Substituting methanesulfonyl chloride for p-toluenesulfonyl chloride, the same method is used to prepare methyl (2S,4S)-1-methanesulfonyl-4-methane-silfonyloxypyrrolidine-2-carboxylate.

EXAMPLE 13

(2S,4S)-$N^2$-Methyl-1-(4-methylbenzenesulfonyl)-4-(4-methylbenzenesulfonyloxy)pyrrolidine-2-carboxamide (XIII R=$CH_3$, $R^2$=$R^4$=p$CH_3C_6H_4$)

Water (400 ml) was saturated with methylamine gas (20 minutes). Title product of the preceding Example (41 g, 89.4 mmol) was added and the resulting slurry stirred for 6 days. Present title product (25.2 g, 62%) was recovered as a white solid by filtration, mp 147°–149° C.; $[alpha]_d^{25}$=–8.70 (c=1.108, methanol); Anal. C 53.25, H 5.24, N 6.05, calcd. C 53.08, H 5.35, N 6.19.

By the same method, the enantiomeric product of the preceding Example is converted to the enantiomer of present title product, and the bis-methanesulfonyl analog of the preceding Example is converted to (2 S,4S)-$N^2$-methyl-1-methanesulfonyl-4-methanesulfonyloxypyrrolidine-2-carboxamide.

EXAMPLE 14

(1S,4S)-2-Methyl-5-(4-methylbenzenesulfonyl)-2,5-diazabicyclo[2.2.1]heptane (VIII, R=$CH_3$, $R^2$=p$CH_3C_6H_4$)

To title product of the preceding Example (2.0 g, 4.42 mmol) in 20 ml tetrahydrofuran was added $LiAlH_4$ (750 mg, 19.9 mmol). The reaction mixture was stirred 24 hours, then quenched by the addition of 3 ml $H_2O$ and 0.75 ml 15% NaOH and extracted 2×15 ml $CH_2Cl_2$. The combined extracts were dried ($MgSO_4$) and stripped to yield 1 g (85%) of title product as a white solid identical with the product of Example 8.

By the same method, the enantiomeric product of the preceding Example is converted to (1R,4R)-2-methyl- 5-(4-methylbenzenesulfonyl)-2,5-diazabicyclo[2.2.1]-heptane, having identical physical properties except for sign of rotation; and the bis-methanesulfonyl analog of the preceding Example is converted to (1S,4S)-2-methanesulfonyl-5-methyl-2,5-diazabicyclo[2.2.1]heptane, identical in physical properties with the product of Example 9.

We claim:

1. A compound of the relative or absolute stereochemical formula

(XVI)

wherein $R^2$ and $R^4$ are each independently ($C_1$–$C_6$) alkyl, trifluoromethyl, or

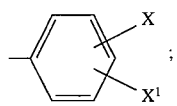

;

X and $X^1$ are each independently hydrogen, ($C_1$–$C_6$)alkyl, bromo, chloro, trifluoromethyl, methoxy or nitro;

$R^8$ is $OR^1$ or NHR; and

R and $R^1$ are each independently ($C_1$–$C_6$)alkyl.

2. A compound of claim 1 of the absolute stereochemical formula (XVI).

3. A compound of claim 1 wherein $R^8$ is $OR^1$ and $R^2$ $R^4$ and are the same and are each methyl or 4-methylphenyl.

4. A compound of claim 2 wherein $R^8$ is $OR^1$, and $R^2$ and $R^4$ are the same and are each methyl or 4-methylphenyl.

5. The compound of claim 4 wherein $R^1$ is ethyl and $R^2$ and $R^4$ are each 4-methylphenyl.

6. The compound of claim 4 wherein $R^1$ is ethyl and $R^2$ and $R^4$ are each methyl.

7. A compound of claim 1 $R^8$ is NHR and R is methyl.

8. A compound of claim 2 wherein $R^8$ is NHR and R is methyl.

9. A compound of claim 7 wherein $R^2$ and $R^4$ are the same and are each methyl or 4-methylphenyl.

10. A compound of claim 8 wherein $R^2$ and $R^4$ are the same and are each methyl or 4-methylphenyl.

11. The compound of claim 10 wherein $R^2$ and $R^4$ are each methyl.

12. The compound of claim 10 wherein $R^2$ and $R^4$ are each 4-methylphenyl.

* * * * *